United States Patent [19]

Ellmann et al.

[11] Patent Number: 4,909,091
[45] Date of Patent: Mar. 20, 1990

[54] METHOD AND APPARATUS FOR THE DETECTION OF CORROSION OR THE LIKE

[75] Inventors: Josef Ellmann, Stutensee; Helmut Stripf, Leopoldshafen; Gunther Krieg, Karlsruhe, all of Fed. Rep. of Germany

[73] Assignees: Kernforschungszentrum Karlsruhe GmbH; Pipetronix GmbH, both of Karlsruhe, Fed. Rep. of Germany

[21] Appl. No.: 120,551

[22] Filed: Nov. 13, 1987

[30] Foreign Application Priority Data

Nov. 14, 1986 [DE] Fed. Rep. of Germany ....... 3638936

[51] Int. Cl.⁴ ..................... G01N 17/00; G01N 27/90; G01N 29/04
[52] U.S. Cl. ........................ 73/866.5; 73/86; 73/865.8; 73/592; 73/623; 73/638; 324/220; 324/207.23; 364/507; 422/53
[58] Field of Search ................ 73/866.5, 86, 622, 623, 73/637, 638, 640, 592, 865.8; 324/208, 220, 221; 422/53; 364/507

[56] References Cited

U.S. PATENT DOCUMENTS

| | | | |
|---|---|---|---|
| 3,495,546 | 2/1970 | Brown et al. | 73/866.5 X |
| 3,636,778 | 1/1972 | Huffstetler | 73/622 |
| 3,786,684 | 1/1974 | Wiers et al. | 73/866.5 |
| 3,967,194 | 6/1976 | Beaver et al. | 324/220 |
| 4,055,990 | 11/1977 | Topping | 73/623 |
| 4,162,635 | 7/1979 | Triplett et al. | 73/623 |
| 4,292,588 | 9/1981 | Smith | 324/221 |
| 4,353,257 | 10/1982 | Urba et al. | 73/592 X |
| 4,507,608 | 3/1985 | Flach, deceased et al. | 324/220 |
| 4,644,336 | 2/1987 | Mark, Jr. | 324/220 X |
| 4,646,012 | 2/1987 | Feilchenfeld et al. | 324/208 |
| 4,807,484 | 2/1989 | Goedecke | 73/865.8 |

FOREIGN PATENT DOCUMENTS

| | | | |
|---|---|---|---|
| 2545370 | 4/1977 | Fed. Rep. of Germany | 324/220 |
| 43481 | 4/1977 | Japan | 324/220 |
| 122101 | 9/1980 | Japan | 324/208 |
| 42137 | 4/1981 | Japan | 73/592 |
| 83607 | 4/1987 | Japan | 73/592 |
| 2140561 | 11/1984 | United Kingdom | 73/622 |

Primary Examiner—Tom Noland
Attorney, Agent, or Firm—Antonelli, Terry & Wands

[57] ABSTRACT

A method and an apparatus for the detection of corrosion, pitting or the like in pipelines is proposed and measured results produced in an appropriate manner are digitally converted, linked with measured values concerning the place and azimuth of the individual sensors to form individual blocks, which are intermediately stored to form larger units and are finally stored in a mass store.

24 Claims, 5 Drawing Sheets

METHOD AND APPARATUS FOR THE DETECTION OF CORROSION OR THE LIKE

BACKGROUND OF THE INVENTION

The invention relates to a method and apparatus for the detection of corrosion, pitting, or the like in pipelines whereby, measurements are performed during the travel of a scraper, with the measurement results being stored and evaluated after carrying out the test run, with the apparatus having at least one measuring unit, a processing unit and a recording unit.

In the case of pipelines, an automatic non-destructive testing in connection with corrosion, pitting or the like is necessary. Such faults and defects can be detected by the changes to the thickness of the pipe wall caused by them.

In connection with crack testing and inspection, the eddy current method has been proposed, in which an alternating electromagnetic field of an exciter coil induces eddy currents in the pipeline wall, which are detected by a sensor coil located at the same point. This method has proved satisfactory for the detection of internal cracks, but is unable or is only able with difficulty to discover defects passing from the outer to the inner wall, such as corrosive wall erosion and cracks, due to the generally considerable thicknesses of the pipe walls (approximately 20 mm and more) and the limited penetration depth of the field. A known apparatus operating according to this method is unsuitable for corrosion detection and was also not used for this purpose.

The use of the stray flux method has also been proposed, in which the pipeline wall is magnetized close to magnetic saturation by the use of permanent magnets or electromagnets. The magnetic field locally passes to the outside through cracks in the pipeline wall. The detection of the stray field using suitable magnetic field sensors makes it possible to detect cracks. However, this process is more suitable for detecting cracks than for corrosion measurements and in particular it is not possible to determine the residual wall thickness of pipelines.

Another method is based on the electromagnetic coupling of ultrasonic waves into the pipeline wall and the measurement of the time delay of the ultrasonic pulses reflected on the back wall. Although no ultrasonic coupling medium is required, the method still requires a high power level for coupling in purposes and has a poor efficiency in converting electromagnetic energy into sound energy, so that the signal-to-noise ratio is too low for the requisite fault detection. This method also does not permit wall thickness determination in connection with internal corrosion.

SUMMARY OF THE INVENTION

The aim underlying the present invention essentially resides in providing a method and an apparatus for permitting the detection of internal and external corrosion, pitting or the like over the entire circumference and length of a pipe wall and with a high degree of precision.

According to the invention, a method for the detection of corrosion or the like in pipelines is solved by means of ultrasonics or eddy current field, whereby during the travel of the scraper measurements are performed, with the measured results being stored and evaluated after performing the test run, wherein individual measurements are performed in timed manner, the measured results are digitized as data, provided with a path length information, intermediately stored and blockwise finally stored.

As a result of the timing of the measurements, there is no need to continuously take and record all the measured values, this only being necessary in the rhythm of the timing, which is dependent on the desired resolution and also on the ratio of the measuring section to be covered and the storage capacity. Through the digitization of the measured results, the requirements are satisfied for storing the same in storage space-economizing form and optionally and additionally to prepare the same. This intermediate, temporary or buffer storage and solely blockwise final storage permits a dense packing of the information on the final storage medium, namely a mass memory or store, which is not the case with the continuous storage of received data.

According to a preferred development of the inventive method, in the case of several measurements made over the circumference of the scraper, they are all combined in a data block with further information. When sensors are distributed over the entire circumference of a test scraper, there is no need to provide the data of each individual sensor with a distance information. It is sufficient if the measured results of the sensors scanned during a scanning period in the multiplex method are combined and provided in overall manner with a distance information. This is more particularly the case if, as described in German patent application P 36 26 646.9, corresponding to commonly assigned co-pending U.S. Application Ser. No. 082,214, filed Aug. 6, 1987 and now U.S. Pat. No. 4,807,484, the sensors sensing the circumference are not all arranged on a circumferential line and are instead successively displaced with respect to one another in groups, so as to be able to uninterruptedly sense the circumference. In this case, it is possible to carry out a correction with respect to a circumferential line for the sensors not located thereon with a view to the distance information.

Even in the case of scrapers which have an eccentric weight distribution, so that they essentially assume the same azimuth position, they can fluctuate about the standard position. Therefore it is also advantageous for the angular position of the scraper in the pipeline to be also determined and stored, so that each measured value with respect to the pipeline circumference can be associated with its correct location. This configuration also saves an eccentric weight distribution if the angular position can be measured over the entire circumference. Preferably a 360° pendulum potentiometer is provided for this.

According to another preferred development the distance information is measured several times and the most probable value is stored. During distance measurements, for which purpose generally odometer wheels are used, it is possible for errors to occur due to the slip or free rotation of a wheel, e.g. in the vicinity of connection pieces. It is therefore appropriate to initially acquire the distance information several times and then to use the most appropriate information for further processing when the information does not coincide. For this purpose several displacement transducers are provided with a distance processing unit and in particular three odometer wheels are uniformly distributed around the circumference. In the case of information relating to two distances, it is fundamentally possible to take the mean value, but as the most frequently occurring error is slip, in preferred manner the value showing the greatest distance is preferably further used, because the value has the smallest slip error. However, the choice can also be coupled with further criteria, such as e.g. the difference between the information relating to the two distances obtained.

Fundamentally several evaluation modes are also possible when information regarding three distances is obtained. Advantageously in the case of three odometer rolls, two odometer wheels are chosen, whose measured results have the smallest difference. In order to correct the odometer counting pulses, it is initially possible to use welds on the pipeline. To the extent that this is possible, outside the pipe and at geodetically precisely known locations, marks, i.e. so-called bench marks can be provided. The signals emitted by them are detected by a receiver when the scraper passes by and stored. These mark signals correct the odometer values during evaluation.

When carrying out measurements, preferably only those measured results are taken and further processed, which are received within a predetermined time range after emitting a measurement or test signal. This makes it possible to eliminate errors, such as can occur through multiple reflections, e.g. when performing ultrasonic measurements. The time intervals can be set in accordance with the forward travel distance or in accordance with the maximum wall thicknesses. It is possible to separately set both the start and finish of the time intervals of the forward travel and wall thickness delay times. This for example ensures that the second rear wall reflection is not used for evaluation purposes. Prior to the scraper movement, the means must be set in such a way that they cover the entire expected pipe wall thickness range.

According to another preferred embodiment, ultrasonic signals are emitted and the time up to the reception of the signals reflected by the front and rear of the pipeline wall is measured.

The ultrasonic delay time measurement takes place according to the pulse reflection process by vertical irradiation. The ultrasonic pulse triggered at the test head by the transmission pulse passes through an oil advance section formed on the test head, is partly reflected on the pipe inner wall, partly passes into the pipe wall and is reflected on the outer pipe wall. Both reflection pulses return to the test head. Multiple reflections can be eliminated during the measurement by corresponding windows. Thus, during this process two delay times or time delays are determined for each emitted ultrasonic pulse, whereof the first gives the distance from the pipe inner wall, while the difference between the two determines the thickness of said inner wall. The two pulses make it possible to establish whether a weakening of the pipe wall is due to internal or external corrosion.

In addition or as an alternative thereto, a low frequency, electromagnetic alternating field can be introduced into the pipe wall and with respect to amplitude, can be detected at a distance from the introduction point and the phase displacement can be measured. In this so-called distant field eddy current method the low frequency, sinusoidal alternating electromagnetic field produced by the exciter coil is passed over the pipeline wall with frequencies of 50 to 500 Hz and is detected by sensors, which are located along the wall with a given spacing and are in particular axially spaced from the exciter coil. This permits a sensitive fault or error detection by measuring the phase displacement between the sine-wave signal to the transmission coil and the sine-wave signals received by the sensors. This method can in particular be used for detecting pitting, but also for determining cracks. The detection of natural corrosion and also welding joints is possible with high sensitivity on both the inside and outside. Preferably induction coils or Hall generators are used as sensors.

The aforementioned measures with regards to the acquisition of data mean that, despite the large amount of information obtained, suitable mass stores in the gigabyte range can store measurements over an adequate distance of several hundred kilometers. In order to be able to finally store even greater distances up to and exceeding 1000 kilometers using gigabit mass stores, such as magnetic tapes, according to a further development of the invention the data are compressed in such a way that with respect to a measured value only following values diverging within a given framework are counted and are determined and stored as a function of their number. In place of a predetermined limit up to which one of the following measured values can diverge, but to ensure interpretation and therefore counting in accordance with the first measured value, according to a special development the numbers of measured values is only counted when the same as the preceding measured value.

According to another preferred embodiment, the final storage of intermediately stored data takes place much more rarely than intermediate storage. As a result of the intermediate storage and the transfer of larger data blocks of the order of magnitude of 1 Mbyte to the mass storage, it is ensured that, compared with continuous recording, the data can be stored much more densely on the storage and therefore a larger data quantity can be stored.

For evaluation purposes, preferably the pipe wall defects are recorded according to the distribution thereof over the wall and in particular different depths of the faults or defects can be recorded with different colors.

In order to be able to establish the cross-section of corrosion or pitting points, according to a preferred development cross-sectional representations of the pipe wall faults are recorded and in particular several section planes are represented in juxtaposed manner.

According to further developments, measurements and the processing of measured values only take place with a finite speed and in addition there is no processing of measurements below a predetermined scraper speed.

BRIEF DESCRIPTION OF THE DRAWINGS

The invention is described in greater detail hereinafter relative to a non-limitative embodiment and the attached drawings, wherein:

FIG. 3b is a resulting cross-section representation of FIG. 3a;

DETAILED DESCRIPTION OF THE INVENTION

With the exception of an externally connectable terminal 18, the inventive measuring and storage means generally designed by the reference numeral 1 is housed in the casing of a scraper, which is moved by pressure difference through a pipeline. The measuring and storing means 1 has a measuring system 2, which can be an ultrasonic and/or an eddy current measuring system, or some other measuring system (FIG. 4).

Figures 1A, 1B, 7:
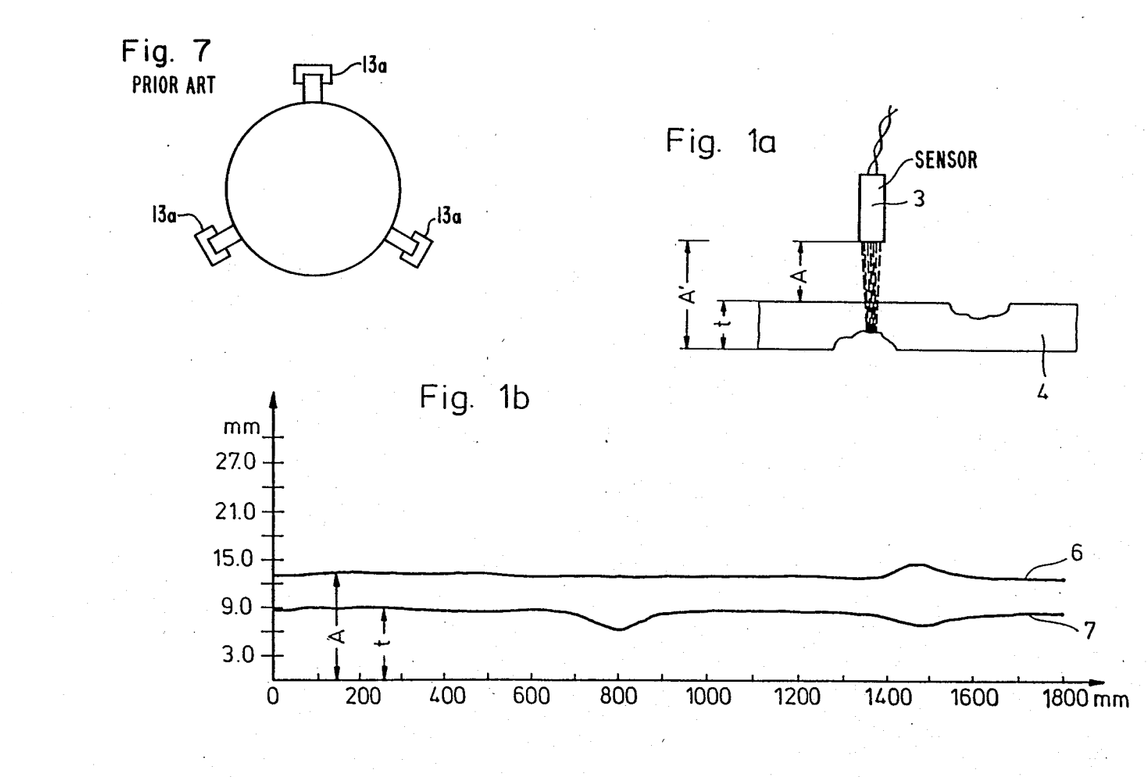
FIG. 1a is a schematic representation of a measuring arrangement for measuring by ultrasonics.
FIG. 1b is a diagrammatic illustration of a sensor wall or wall thickness spacing.
FIG. 7 is a diagrammatic sketch depicting the disposition of odometer rolls in the scraper arrangement of FIG. 5.
Figure 5:
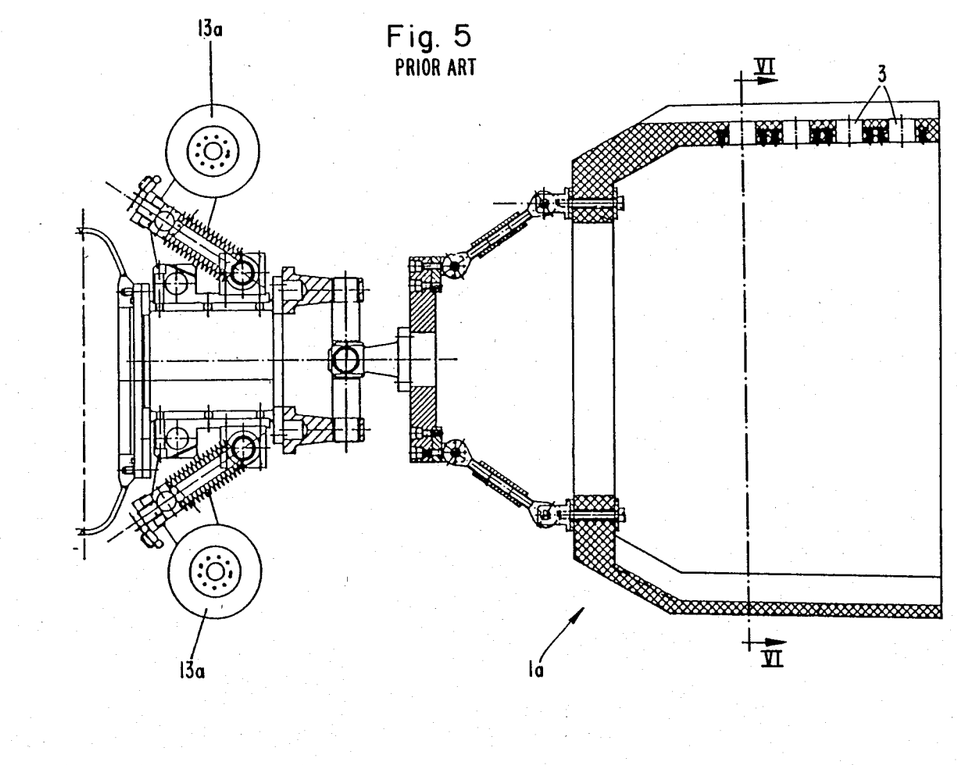
FIG. 5 is a side view of a scraper arrangement.
Figure 6:
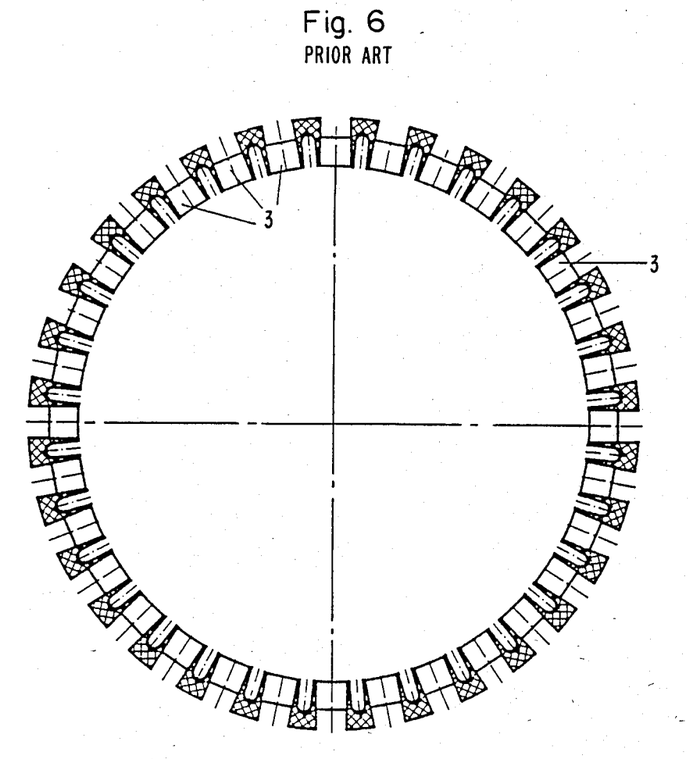
FIG. 6 is a cross sectional view taken along the line VI—VI in FIG. 5.

For example, several ultrasonic sensors 3 (FIG. 1a) are appropriately arranged over the circumference of the scraper as shown most clearly in FIGS. 5 and 6. Electronic channels associated with the sensors 3 are interrogated in the multiplex process. An ultrasonic signal emitted against a wall 4 is firstly reflected on the surface directed towards the sensor 3, i.e. the front wall, as a first measured or test signal 6, which indicates the spacing of the sensor 3 and wall 4 and is then reflected on the back of the wall 4 as a further measured or test signal, the time delay difference giving a measured or test signal 7 for the wall thickness t (FIG. 1b). In FIG. 1b, initially only test signal 7 has a divergence from the normal value and therefore indicates the reduction of the wall thickness t at the point marked "outside" in FIG. 1a, whereas signal 6 indicating the spacing A between sensor 3 and wall 4 shows no change. However, at the second corrosion point marked "inside" in FIG. 1b, in test signal 6 also has a divergence, in the same way as test signal 7. Test signal 6 here shows the change to the sensor-wall spacing A and therefore indicates that there is internal corrosion, while test signal 7 again gives the complete wall thickness t.

Figure 2A:
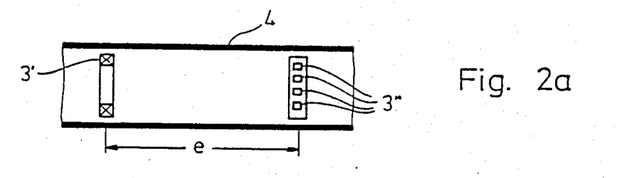
FIG. 2a is a schematic representation of an eddy current measuring arrangement.
Figure 2B:
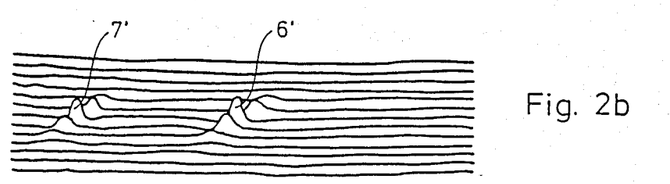
FIG. 2b is a diagrammatic illustration of measured results of an eddy current measurement over an inspected surface.
Figure 3A:
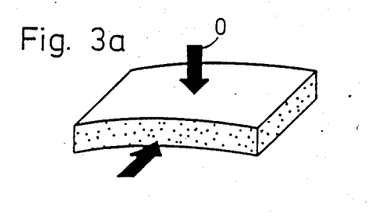
FIG. 3a is a diagrammatic illustration of two representation modes.
Figure 3B:
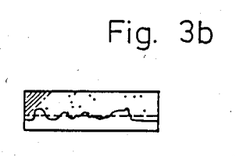
Figure 3C:
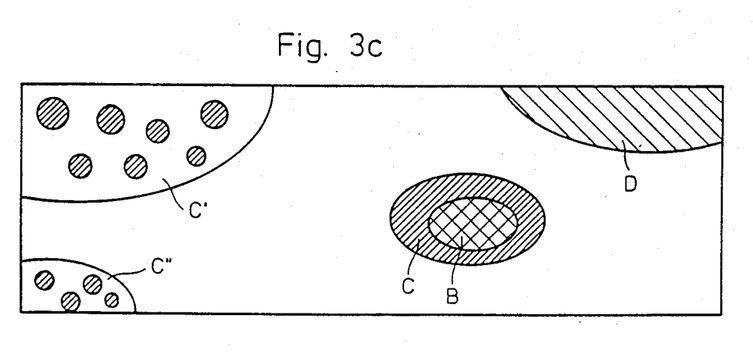
FIG. 3c is a measurement in a real general view.

FIG. 2a diagrammatically shows the arrangement of an exciter coil 3' and its associated sensors 3" in a pipeline with wall 4. FIG. 2b shows the delay signal obtained, i.e. the phase shift between the exciter signal and the sensor signal, the peaks 6', 7' indicating damaged points on pipe wall 4. A recording curve gives a longitudinal section through the pipe wall (arrow O in FIG. 3a), while the curves indicate the change over the azimuth. FIG. 3b is a cross-sectional representation for an ultrasonic signal, while FIG. 3c is an areal view corresponding to arrow O in FIG. 3a. Different wall thicknesses can be reproduced by different patterns or color applications. Area B e.g. shows in dark red a deep hole, which is surrounded by a somewhat flatter area C in yellow. In area C', C' there are numerous individual holes of the same depth (yellow), while area D has flat unevenesses in blue. It is possible to make fine gradings, e.g. by color applications. The standard wall thickness is represented by the background color. It is not possible to reproduce the color codings here and they can only be explained in the aforementioned manner.

Figure 4:
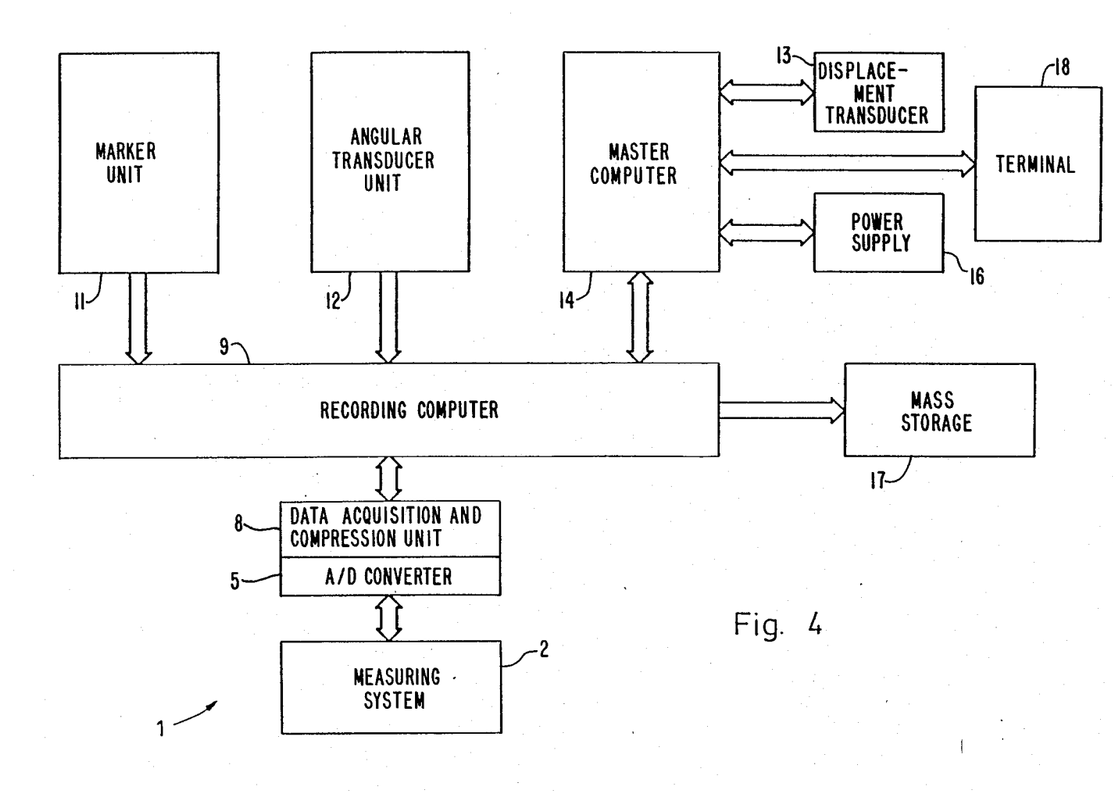
FIG. 4 is a block circuit diagram of the apparatus according to the invention.

The partial methods resulting from the measurement, data acquisition, optionally data compression, recording and control operations are processed by several processor systems associated with each of the partial methods, namely, A/D converter 5, data acquisition and compression unit 8, recording computer 9 and master computer 14 (FIG. 4). The different computer systems communicate with one another via bus or parallel coupling.

Measuring system 2 is followed by a data acquisition and compression unit 8, which can also have a module for data compression purposes. The acquired data are transferred to a recording computer 9, which has a buffer store. In the data acquisition and compression unit 8, the acquired data are linked with further data, particularly the location of the scraper and its angular position in the pipe. For this purpose there is a marker unit 11, an angular transducer unit 12 and a displacement transducer unit 13. In order to relieve the data acquisition and compression unit 8, the additional data are timed, are detected by the displacement transducer 13 via recording computer 9, and are linked with the other test data via a dual port-RAM from the recording computer 9. The overall control of the inventive means is via a master computer 14. In the test phase, the master computer 14 can poll and represent the acquired data from recording computer 9. At the end of a scraper travel, the magnetic tape is connected to a personal computer in order to read and evaluate the data.

By a counter and timer timed by the data acquisition and compression unit 8, e.g. ultrasonic generators are activated in such a way that ultrasonic pulses are emitted with a time interval of less than 100 $\mu$s, e.g. every 39 or 78 $\mu$s. The sensors are operated sequentially while maintaining an angular displacement of approximately 175°, so that there is a minimum reciprocal influencing of the individual sensors. In the case of sixty-four sensors distributed over the scraper circumference and a pulse emission every 78 $\mu$s, there is a total scan time over the circumference of 5 milliseconds, so that in the case of an average scraper speed of 1 m/sec, the distance between two scan points in the longitudinal direction is 5 mm. On reducing the pulse scan time to 39 $\mu$s, the pulse-distance spacing can be reduced to 2.5 mm, so that in the case of a scan diameter of 6 mm in the longitudinal direction, it is reliably possible to ensure a complete surface-covering scan. In the case of a scan frequency of 12.8 kHz (operation every 78 $\mu$s), as a result of the aforementioned two reflected test signals, on the front and rear pipeline wall surfaces there is a data rate of 25,600 measured values per second. In the case of the aforementioned scraper speed, these data occur for a period of 83 hours, e.g. with a 300 km long pipeline. The time delay of the reflected signals is digitized with the aid of a time delay counter, which is e.g. timed with 29.6 mHz, so that there are resolutions of the ultrasonic system of 0.1 mm in the pipe wall and 0.021 mm in the space between the sensor and the wall. As smaller resolutions are adequate, the data can e.g. be recorded with a resolution of 0.2 mm wall thickness and 0.33 mm in the intermediate space. Thus, for an 8 bit digital representation for each measured value, there is a maximum detectable wall thickness of 51 mm and a spacing of 82 mm, which is completely adequate.

The above information reveals the high data transmission rate and the total information obtained over the exemplified test run.

The pulse repetition frequency and therefore the number of sensors, together with the total scan frequency, for the given, desired resolution is initially determined by the maximum data rate of the final storage, namely, a mass store, such as a magnetic tape, which can be 1.6 Mbit/sec.

In order to reduce the data rate and information quantity supplied by the data acquisition and compression unit 8, in preferred manner a data compression takes place. This is effected in that, instead of separately storing each measured value, following the measurement of a value and, in particular, the standard values of wall spacing and thickness of the pipeline, similar or identical values are merely counted. Similar or identical means that the following values only differ by a preselectable amount from the starting value and then only need be counted as similar or identical values. It is then only necessary to store the number of identical or similar measured values until a value exceeding the given limit occurs. The number of identical or similar measured values can take place in that in a digital word repesenting a measured value, e.g. a byte, the most significant bit is not used for representing the measured value. This can then be separately set if a measured value is the same or similar to a preceding measured value, so that during evaluation there is a different interpretation of the word or byte. In the least significant bits are recorded the number of measured values which, compared with the last measurement, have differed by one maximum predetermined value. If a byte is still used as the word, then in this form a maximum of 128 measured values can be counted as identical or similar. If there are fewer measured values, then in a following byte the most significant bit is not set, so that the following byte is again interpreted as a measured value.

In order to be able to scrape longer pipelines with a larger number of sensors, the compression factor can be further improved. Additional use is made of the mode "difference smaller than 16". If the difference corresponding to the measured value is smaller than 16, then two measured values can be separately represented in one byte. The mode and the number of bytes therein is recorded in a commander guide byte.

Apart from the depth of the corrosion points, during evaluation, interest is also attached to their location and extension. A scraper generally designed by the reference numeral 1a (FIG. 5) is forced through the pipeline through the medium of the latter or the pressure difference upstream and downstream, so that its speed can change. Therefore a distance or path measurement is performed and measured data and distance are associated with one another. For this purpose a displacement transducer unit 13 or an odometer system is provided, which receives distance pulses from several odometer wheels 13a (FIGS. 5 and 7). As errors can occur due to slip effects or free-wheeling odometer wheels 13a within T-sections of the pipeline, it has proved advantageous in the case of several odometer wheels 13a to form the mean value of the closest distances. This makes it possible to minimize errors. Electronic markers can be provided along the pipeline for distance calibration purposes or they can be set up during the travel of the scraper 1a. The signals emitted by the markers are detected by the master unit 11 when the scraper 1a passes by and are supplied to the recording computer 9.

For the clear definition of the azimuth position of the scraper 1a, which is necessary for locating the corrosion over the pipe circumference, use is made of a 360° pendulum potentiometer and an analog-digital converter 5.

Master computer 14 monitors the remaining electronic components and is programmed in distance-dependent manner by the displacement transducer 13. Preferably the power supply 16 of the master computer 14 is independent of the supply for the remaining electronics, so that it can monitor the power supply for the remaining components. A non-volatile store or memory is provided for storing faults and errors which occur.

In order to ensure synchronization, i.e. the retrievability of the individual data, particularly in connection with the distance covered until they occur, the data of marker 21, angular transducer unit 12, such as, for example, a pendulum potentiometer, the displacement transducer 13, as well as measured temperature data and the data of measuring system 2 within a measuring period, i.e. the data detected during a total scan time for all the measurement points distributed over the scraper circumference are combined to data blocks at the front and rear wall surface and the individual blocks can be identified. There are three bytes for the distance information, so that in the case of an adequate resolution of 10 cm, e.g. 1677 km can be detected. Independently of whether or not the data are compressed, they are transmitted by the data acquisition and compression unit 8 to the recording computer 9, coupling taking place by a dual port-RAM as the interface between the data acquisition and the recording. After being provided with an identification code, the data are initially intermediately stored in a buffer store of e.g. 1 Mbyte and from there are transmitted by direct memory access in the form of transmission blocks with e.g. a size of 512 Kbyte to the large mass storage 17, such as a magnetic tape with 40 gigabit at a transmission rate of e.g. 400 Kbit and this takes place in a serial-synchronous manner. The latter is only limited by the maximum recording rate of the mass storage 17, which in the case of the tape recorder used is approximately 1.6 Mbits per second.

Apart from the preprocessing of the data prior to the final recording, also for reasons of utilizing the tape recorder capacity, the data are not continuously transferred thereto and instead this takes place blockwise. Undefined data zones occur on the tape during the starting and running phase as a result of the start-stop operation. Thus, in each case, a transferred block is 512 Kbyte.

When the run is completed, the stored data can be evaluated. A first realization mode of the evaluation comprises the provision of only those measured values, whose amounts are within a predeterminable size range. With regards to the ultrasonic measurement, this means that values are indicated which are below a given minimum wall thickness. In the case of the eddy current method, only those phase displacements would be supplied which were larger than a minimum phase displacement.

In another detailed evaluation procedure the surface distribution of the measured corrosion points on the inner face of the pipe is recorded, different corrosion depths being given different color values and there is a quantitative graphic representation in longitudinal section of corrosion and crack regions which are of interest.

What is claimed is:

1. A method of detection of corrosion or the like in pipelines by selective use of at least one of ultrasonics or eddy current field, whereby during travel of a scraper apparatus, test run measurements are performed, measured results are stored and said measured results are evaluated after performing the test run, wherein individual measurements are performed in a timed manner, the measured results are digitized as data, provided with a path length information, intermediately stored, and finally stored in data blocks.

2. A method according to claim 1, wherein several measurements are performed over the circumference of the scraper apparatus, and the measurements are combined in a data block with further information.

3. A method according to claim 1, wherein an angular position of the scraper apparatus in the pipeline is determined and stored.

4. A method according to claim 1, wherein the path length information is measured several times and the most probable path length information is stored.

5. A method according to claim 4, wherein the path lengths are measured by three odometer rolls, differences of measured path lengths are determined.

6. A method according to claim 1, wherein signals emitted at predetermined locations on the pipe are detected by sensing means carried by the scraper apparatus and the signals correct the path length information given odometer rolls during evaluation.

7. A method according to claim 1, wherein only those measured results are taken and further processed, which are received within a predetermined time interval following the emission of a test signal.

8. A method according to claim 1, wherein ultrasonic signals are emitted and the time up to a reception of time delay signals reflected by a front wall and a rear wall of the pipeline is measured and the time difference between the two time delay signals is retained.

9. A method according to claim 1, wherein a low frequency alternating electromagnetic field is introduced into the pipewall, and detected at a certain distance from a point of introduction of the electromagnetic field into the pipewall, and a phase shift between emitted and detected signals is measured.

10. A method according to claim 1, wherein data compression takes place during data acquisition.

11. A method according to claim 10, wherein the test run data are compressed in such a way that only those measured values differing within a predetermined range from a preceding value are counted and their number is established and stored.

12. A method according to claim 11, wherein the number of identical measured values following a particular measured value is determined.

13. A method according to claim 10, wherein only the difference between corresponding measured values is stored.

14. A method according to claim 13, wherein, in the case of measured value differences below a predetermined value, several measured values are separately represented in a single byte and wherein, in a guiding byte, the mode and number of bytes contain several measured values.

15. A method according to claim 10, wherein a definite bit of a digital value is used for identification of the information mode contained in the value.

16. A method according to claim 1, wherein the final storage of intermediately stored data takes place much more rarely than intermediate storage.

17. A method according to claim 1, wherein pipe wall defects are recorded in accordance with their distribution over the wall.

18. A method according to claim 17, wherein different depths of the defects are marked with different colors.

19. A method according to claim 1, wherein cross-sectional representations of pipe wall defects are recorded.

20. A method according to claim 19, wherein several sectional planes are represented in directly juxtaposed manner.

21. A method according to claim 1, wherein measurements and the processing of measured values only occur in the case of a non-zero scraper apparatus speed.

22. A method according to claim 21, wherein no processing of measurement takes place below a predetermined scraper apparatus speed.

23. A method according to claim 1, wherein the energy supply is continuously monitored.

24. A method according to claim 1, wherein for a first evaluation only measured values over a predetermined wall thickness divergence are further processed.

* * * * *

UNITED STATES PATENT AND TRADEMARK OFFICE
CERTIFICATE OF CORRECTION

PATENT NO. : 4,909,091

DATED : Mar. 20, 1990

INVENTOR(S) : Ellmann et al.

It is certified that error appears in the above-identified patent and that said Letters Patent is hereby corrected as shown below:

On the title page, the inventors should read as follows:
[75] Inventors:  Josef Ellmann, Stutensee; Helmut Stripf, Leopoldshafen; Gunther Krieg, Karlsruhe, Wolfgang Krieg, Stutensee, Dr. Josef Ottes, Bruchsal, all of Fed. Rep. of Germany Signed and Sealed this Thirtieth Day of June, 1992

*Attest:*

DOUGLAS B. COMER

*Attesting Officer*    *Acting Commissioner of Patents and Trademarks*